United States Patent
Weinberger

(10) Patent No.: US 6,258,072 B1
(45) Date of Patent: Jul. 10, 2001

(54) CATHETER PROTECTIVE DEVICE

(75) Inventor: Judah Weinberger, Teaneck, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/292,093

(22) Filed: Apr. 14, 1999

(51) Int. Cl.⁷ .................................................. A61M 25/00
(52) U.S. Cl. .............................................. 604/284; 604/256
(58) Field of Search .................................. 604/523, 264, 604/284, 256, 247, 164, 171

(56) References Cited

U.S. PATENT DOCUMENTS 5,843,046 * 12/1998 Motisi et al. ................... 604/247 X \* cited by examiner

*Primary Examiner*—Manuel Mendez
(74) *Attorney, Agent, or Firm*—Cowman, Liebowitz & Latman, P.C.; William H. Dippert

(57) ABSTRACT

This invention concerns a catheter protective device useful for a Y-adaptor, where a tubular member is positioned at the proximal end of the Y-adaptor The tubular member protects a catheter from being crushed by a fastener on the Y-adaptor and minimizes blood bleed-back.

9 Claims, 2 Drawing Sheets

CATHETER PROTECTIVE DEVICE

FIELD OF THE INVENTION

This invention is directed to a catheter protective device. More particularly, this invention is directed to a device for protecting the proximal sections of catheters and minimizing blood loss during catheter exchanges.

BACKGROUND OF THE INVENTION

During certain invasive intravascular procedures such as percutaneous transluminal coronary angioplasty (PTCA), a number of devices are inserted into and removed from the patient's cardiovascular system through an opening, for example, in the femoral artery. In a typical procedure, a guide catheter with a diameter of approximately 8 French will be advanced distally within the patient's arterial system and then a guidewire will be advanced within the guide catheter, to the point that the distal portion of the guidewire will be maneuvered to a point distal to the distal end of the guide catheter. Then, dependent upon the particular procedure being performed, one or more different catheters will be advanced over the guidewire, including situations where one catheter may be "exchanged" for another over the guidewire.

Typically at the proximal end of the guide catheter there will be a "Y" adaptor having two or more manifolds or ports for the introduction of and removal of guidewires, catheters, and the like. In some instances an additional Y-adaptor may be linked to another Y-adaptor.

One characteristic of the Y-adaptors is that they are preferably able to tighten, that is, "clamp down", onto a device such as a catheter to be inserted, to hold the catheter in position as well as to minimize blood leakage and to allow simultaneous monitoring of blood pressure. Existant Y-adaptors have the drawback that they sometimes will damage expensive, mechanically fragile catheters when the clamp is tightened or inhibit intracatheter movement. In addition, there may be a significant blood loss, particularly during certain catheter exchanges.

In recognition of the aforementioned problems at least one company has developed a modified Y-adaptor that has an O-ring arrangement. However, that arrangement is specific to that one particular company's Y-adaptor. Also, some cardiologists have adopted commercially available Y-adaptors by adding additional O-rings to minimize bleed-back during catheter exchanges. However, this is a cumbersome and unacceptable procedure.

OBJECT OF THE INVENTION

It is an object of this invention to provide a catheter protective device.

It is also an object of this invention to provide a device for minimizing damage to catheters that are secured by Y-adaptors in vascular procedures.

It is a further object of this invention to minimize blood loss during certain intravascular procedures.

It is a yet further object of the converter to provide a simple device for modifying existant Y-adaptors to reduce blood loss and to minimize catheter damage.

These and other objects of the invention will become more apparent from the description above.

SUMMARY OF THE INVENTION

This invention is directed to a device for protecting catheters, particularly during invasive cardiological procedures. According to the invention, a device is designed to be positioned by control of the proximal portion of a guide catheter. The device comprises a tubular member to be positioned within the proximal portion of a Y-adaptor as well as a Y-adaptor containing such a tubular member. The tubular member is held in position by an annular valvular or locking mechanism. Preferably there is an O-ring or a one-way valve in the annular space between the tubular member and the proximal portion of the Y-adaptor. It is also preferable that the lumen of the tubular member will contain a hemostatic valvular mechanism. Further, preferably the tubular member will comprise a reasonably stiff material that will resist crushing of any catheter or other device that might be inserted through the lumen of the tubular member.

DETAILED DESCRIPTION OF THE INVENTION

Figure 1:
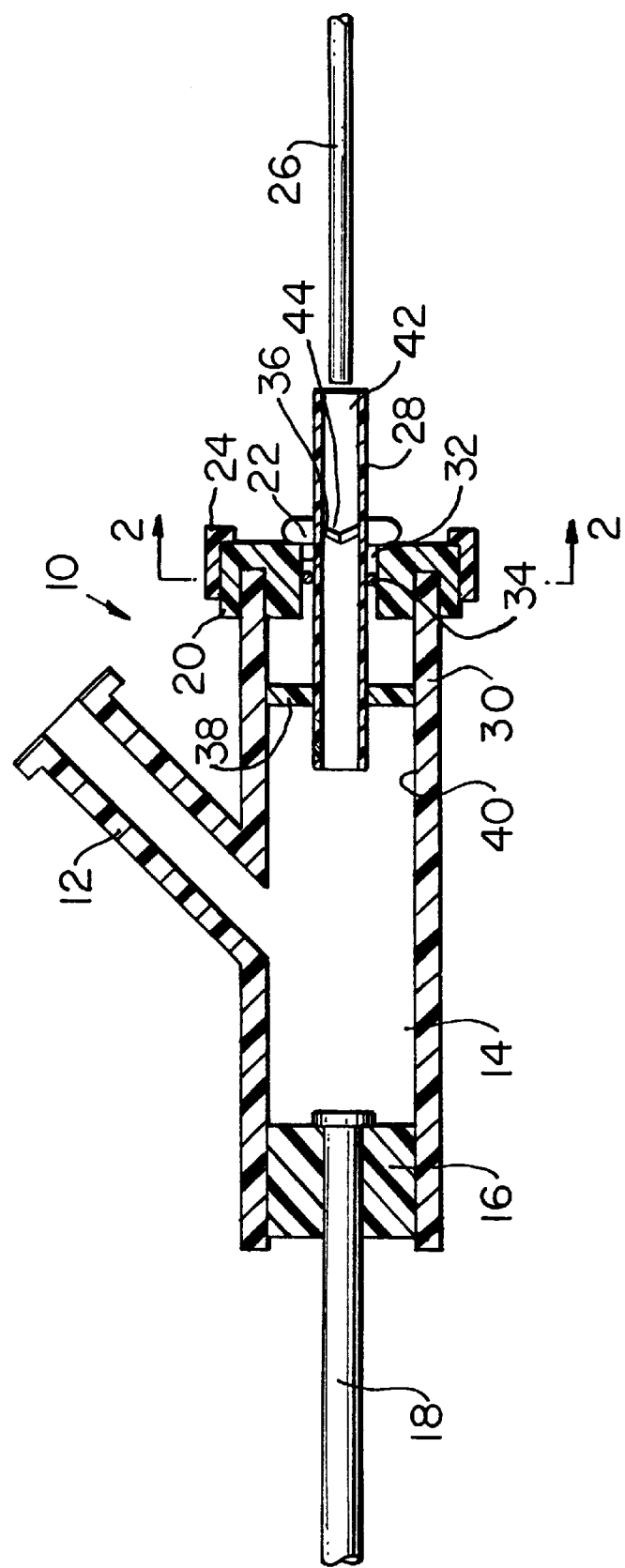
FIG. 1 comprises a schematic, partially cross-sectional view of an embodiment of the invention.

The invention can perhaps be better appreciated by making reference to the drawings. In FIG. 1, a conventional Y-adaptor 10 comprises a manifold accepting member 12, an inner lumen 14, a connector 16, such as a LUER LOK connector, for connecting to a guide catheter 18, a fastener 20, and a proximal opening 22. Fastener 20 typically has a rotable member 24 for reducing the opening 22 to grip a catheter, guidewire, or other device 26 that is inserted into opening 22 and advanced through guide catheter 18.

Figure 2:
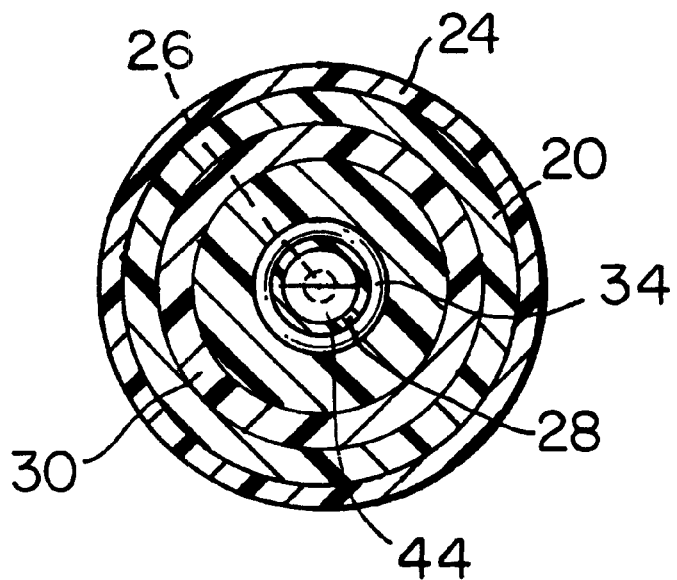
FIG. 2 is a cross-sectional view along line 2—2 of the embodiment of FIG. 1.

According to the invention a tubular member 28 is positioned within the proximal portion 30 of Y-adaptor 10. The tubular member 28 extends proximally and distally of a lumen 32 formed within fastener 20. An annular sealing member 34 is positioned in the annular space between tubular member 28 and the interior surface 36 of fastener 20, as shown in a different view in FIG. 2. Optionally, or alternatively, there may be an annular sealing member 38 in the annular space between the interior surface 40 of Y-adaptor 10 and tubular member 18. A flange 41 rests against fastener 20 and prevents distal movement of tubular member 28.

Sealing members 34 and 38 each preferably comprise an O-ring, a one-way hemostatic valve, or a multileaf valve to prevent blood or other fluid leakage or bleed-back. Lumen 42 of tubular member 18 preferably comprises a one-way hemostatic valve 44.

Tubular member 28 comprises at least one lumen 42 through which a guidewire or an intravascular catheter, represented as 26, could be inserted. Useful intravascular catheters include balloon dilatation catheters, ultrasound catheters, radiation catheters, atherectomy catheters, local drug or radiation delivery devices, and the like.

Figure 3:
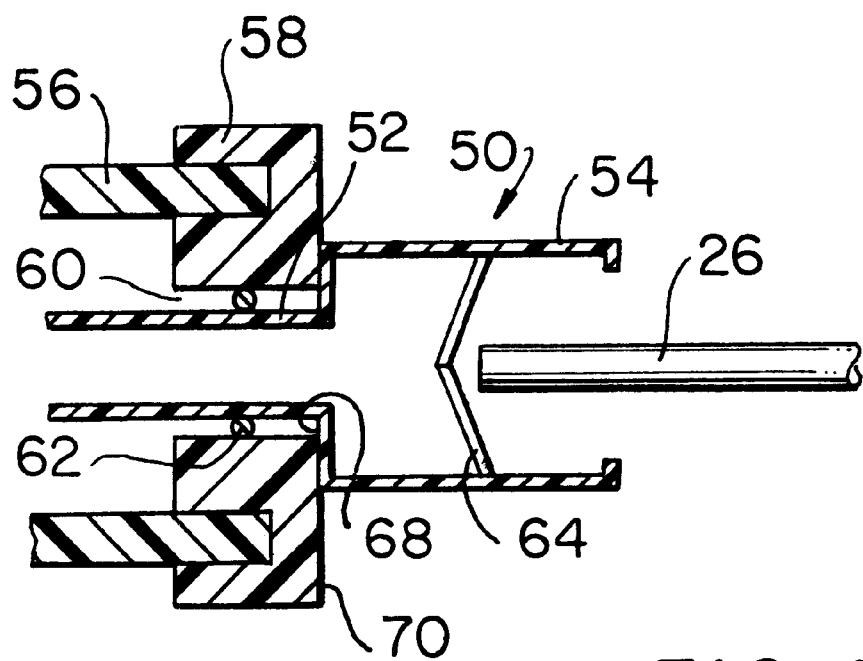
FIG. 3 is a partial, cross-sectional view of another embodiment of the invention.

Another embodiment of the invention is shown in FIG. 3, where a tubular member 50 comprises distal section 52 and proximal section 54. Distal section 52 is positioned within a proximal portion 56 of a Y-adaptor. Proximal portion 56 comprises a rotable fastener 58 having a lumen 60, and distal section 52 extends longitudinally within lumen 60.

An annular sealing member 62 is positioned in the annular space between the interior space surface of fastener 58 and distal section 52. Sealing member 62 preferably comprises an O-ring, a one-way hemostatic valve, or a multileaf valve to prevent blood or other fluid leakage or bleedback.

Tubular member 50 comprises one or more one-way hemostatic valves, in either distal section 52 or proximal section 54, and one or more lumens. Preferably tubular member 50 comprises one lumen with a one-way hemostatic valve 64, as shown, or in proximal section 54. In another preferred embodiment there is a one-way hemostatic valve in each of distal section 52 and proximal section 54.

Proximal section 54, which may have a larger diameter or effective diameter than that of distal section 52, may be circular or non-circular in inner cross-section or outer geometry. In one preferred embodiment proximal section 54 will have a hexagonal or octagonal outer geometry, and a distal surface 68 of proximal section 54 will fit against or engage proximal surface 70 of fastener 58. Proximal section 54 could optionally have a non-uniform shape, such as, for example, a funnel shape.

Tubular member 28 or 50 can be useful in two ways: First, the tubular member can be inserted into a conventional commercially available Y-adaptor, such as the PASSAGE™ Hemostatic Valve, available from Merit Medical Systems. Preferably the tubular member would be inserted into the proximal part of a Y-adaptor prior to initiation of a procedure, e.g., when placing an initial balloon catheter into device 10, although it is possible that it could be inserted during the procedure. The tubular member could be inserted into the proximal port, and then fastener 20 or 58 would be tightened to hold the tubular member in position.

And second, a Y-adaptor could be adapted to integrate tubular member 28 or 50. Such a Y-adaptor could have a tubular member already inserted and positioned within a fastener. optionally no fastener will be required if the tubular member is otherwise fixed in position and catheters, guidewires, and the like are inserted through a lumen of the tubular member and held in position by a hemostatic valve means.

The tubular number will preferably be comprised of one or more suitable physiological acceptable polymers or metals. A polymer for the distal section of the tubular member must have sufficient rigidity to prevent the crushing of a catheter or guidewire. Suitable polymeric materials useful according to the invention include, but are not limited to, polyethylene, polypropylene, and copolymers thereof. Suitable metals include, but are not limited to, stainless steel and nitinol. It is within the scope of the invention that the tubular member may comprise two or more different materials bonded together. For example, the inside might comprise a rigid material whereas the outside may comprise a "softer", less rigid material.

The tubular member is preferably from about 0.5 cm to about 10 cm in length, with an inner diameter of from about 0.2 mm to about 1.0 cm and a wall thickness of from about 0.1 mm to about 5.0 mm. The tubular member can be substantially cylindrical or its diameter could vary from one end to the other. Preferably the end with the smaller diameter could be positioned distally. Where the distal and proximal sections of the tubular member are discontinuous, as in FIG. 3, the total length of the tubular member will be from about 2 cm to about 12 cm, with the ratio of the respective lengths of the distal and proximal sections ranging from about 1:4 to about 10:1. The inner diameter and wall thickness of the distal section will be as described hereinbefore, whereas the inner diameter of the proximal section will preferably be from about 0.5 mm to about 3.0 cm and the wall thickness could range from about 0.1 mm to about 3.0 mm.

Any O-ring or hemostatic valve would be comprised of conventional materials, including, but not limited to, suitable polymeric materials such as silicone or silicone polymer.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. In a Y-adaptor for cardiac or vascular use which comprises a port to engage a guide catheter and at least one additional port to facilitate entry of a catheter or guidewire, the improvement wherein at least one additional port comprises a catheter protection device for a Y-adaptor having a fastener at its proximal end, said catheter protective device comprising a tubular member having at least one lumen therethrough, wherein at least one lumen has a hemostatic valve and said tubular member is capable of being inserted into the Y-adaptor proximal end.

2. The Y-adaptor of claim 1, wherein the tubular member is non-crushable.

3. The Y-adaptor of claim 1, wherein the tubular member has a sealing mechanism to seal any annular space between the tubular member and the fastener.

4. The Y-adaptor of claim 3, wherein the sealing mechanism comprises an O-ring or a one-way valve.

5. The Y-adaptor of claim 1, wherein the tubular member has a flange configured to fit adjacent to the Y-adaptor proximal end.

6. The Y-adaptor of claim 1, wherein the tubular member has proximal and distal sections and the diameter or effective diameter of the proximal section is greater than the diameter or effective diameter of the distal section.

7. The Y-adaptor of claim 6, wherein the distal section is substantially cylindrical.

8. The Y-adaptor of claim 6, wherein the proximal section has a hexagonal or octagonal outer geometry.

9. The Y-adaptor of claim 1, wherein the tubular member has proximal and distal sections each comprised of different material.

* * * * *